United States Patent
Modolo et al.

(10) Patent No.: US 6,312,654 B1
(45) Date of Patent: *Nov. 6, 2001

(54) METHOD OF SEPARATING A TRIVALENT ACTINIDE FROM A TRIVALENT LANTHANIDE AND/OR YTTRIUM IN AQUEOUS SOLUTION

(75) Inventors: Giuseppe Modolo, Jülich; Reinhard Odoj, Gey, both of (DE)

(73) Assignee: Forschungszentrum Julich GmbH, Julich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/508,915

(22) PCT Filed: Sep. 15, 1998

(86) PCT No.: PCT/DE98/02815

§ 371 Date: Mar. 16, 2000

§ 102(e) Date: Mar. 16, 2000

(87) PCT Pub. No.: WO99/14386

PCT Pub. Date: Mar. 25, 1999

(30) Foreign Application Priority Data

Jul. 29, 1997 (DE) ............................................. 198 34 152

(51) Int. Cl.[7] ........................... C22B 59/00; C22B 60/00; C09K 3/00
(52) U.S. Cl. ........................... 423/10; 423/21.5; 252/184
(58) Field of Search .................... 423/10, 21.5; 252/184

(56) References Cited

U.S. PATENT DOCUMENTS 4,162,230 * 7/1979 Horwitz et al. ...................... 423/21.5
4,647,438    3/1987 Sabot et al. .
4,867,951    9/1989 Smith et al. .
5,966,584 * 10/1999 Modolo et al. ........................... 423/7

FOREIGN PATENT DOCUMENTS 0 210 387 A1   2/1987 (EP) .

OTHER PUBLICATIONS

A Review of the Basic Chemistry and Recent Developments in Trivalent Element Separation published in Solvent Extraction 11(4), 729–768 (1993), No month.

The Separation of Trivalent Actinides From Lathanides... published in Journal of Alloys and Compounds 271–273 (1998), No month.

* cited by examiner

Primary Examiner—Steven Bos

(57) ABSTRACT

The invention relates to a method of separating trivalent actinides from at least one trivalent lanthanide and/or yttrium, whereby the trivalent actinides are extracted from an aqueous solution containing a $H^+$ concentration of 0.01 to 2 moles/liter by using as extractant an (aryl)dithiophosphinic acid of the Formula $R_1R_2PS(SH)$, in which $R_1$ is phenyl or naphthyl, $R_2$ is phenyl or naphthyl, or $R_1$ and $R_2$ are each phenyl or naphthyl substituted by methyl, ethyl, propyl, isopropyl, cyano, nitro, or halogen, with addition of an extraction synergist selected from the group consisting of trioctylphosphate, tris-(2-propylpentyl)-phosphate, and tris-(2-ethylhexyl)-phosphate. The use of the synergist in the extraction allows for a more selective extraction.

8 Claims, No Drawings

METHOD OF SEPARATING A TRIVALENT ACTINIDE FROM A TRIVALENT LANTHANIDE AND/OR YTTRIUM IN AQUEOUS SOLUTION

CROSS REFERENCE TO RELATED APPLICATIONS

This application is related to Ser. No. 08/931,894 filed Sep. 17, 1997 now U.S. Pat. No. 5,966,584. This application is the U.S. National Phase of PCT/DE 98/02815 filed Sep. 15, 1998.

FIELD OF THE INVENTION

The invention relates to a method of separating trivalent actinides from at least one trivalent lanthanide using an extraction-medium containing an extractant and an extraction synergist.

BACKGROUND OF THE INVENTION

The separation of trivalent actinides like americium or curium, from trivalent lanthanides has long been a problem. The reason for the difficulties in the separation of these elements is the very close chemical properties of the trivalent ions of the lanthanides and actinides. Especially the very similar ionic radii contribute to similar properties of these element groups. Thus numerous investigations have hitherto been undertaken to separate the trivalent ions of the actinides and lanthanides with the highest possible selectivity and increased efficiency.

It is indeed known that extraction agents with mild donor groups like nitrogen or sulphur as complex formers contain structural components which in liquid-liquid extraction have a certain selectivity with respect to trivalent actinides although up to now such separations have been carried out only at relatively high pH values which tend to precipitate formation of the trivalent actinides or require 10 molar LiCl solutions.

In the publication K. L. Nash, Solvent Extr. Ion Exch. 11 (4), 729–768 (1993) the Talspeak process is described and enables selective extraction of lanthanides with the aid of complexing agents which maintain the trivalent actinides in solution. However, this separating process is also carried out at a relatively high pH value of 3–4 and requires the addition of further salts.

A process developed by the Applicant for the extraction of trivalent actinides from aqueous solutions which contain trivalent actinides and trivalent lanthanides, enables a separation at high acid concentrations of 0.01 to 2 mol/liter $HNO_3$. Following this process, such an aqueous acid solution which contains a mixture of trivalent lanthanides and actinides is extracted by means of an organic solvent. With this process, because of the low pH value or the high acid concentration, a precipitate formation of the trivalent actinides is hindered and good separation results are obtainable. To evaluate the separation results, characteristic values such as the distribution coefficient D and the separation factor α are considered $$D_{An(III)}=[An(III)_{org}]/[An(III)_w] \quad (1)$$

In formula 1:

$D_{An(III)}$=distribution coefficient for a trivalent actinide (dimensionless)

$[An(III)_{org}]$=concentration of the trivalent actinide in the organic phase (mole/liter)

$[An(III)_w]$=concentration of the trivalent actinide in the aqueous phase $$D_{Ln(III)}=[Ln(III)_{org}]/[Ln(III)_w] \quad (2)$$

In formula 2:

$D_{Ln(III)}$=Distribution coefficient for a trivalent lanthanide (dimensionless)

$[Ln(III)_{org}]$=concentration of the trivalent lanthanide in the organic phase (mole/liter)

$[Ln(III)_w]$=concentration of the trivalent lanthanide in the aqueous phase.

$$\alpha=D_{An(III)}/D_{Ln(III)}$$

α=separating factor (dimensionless) depending upon the process, the use of bis(aryl)dithiophosphonic acid in strongly acid medium can produce separating factors α lying between about 20–50.

OBJECT OF THE INVENTION

It is therefore the object of the invention to provide a method for extraction of trivalent actinides from a solution containing at least one trivalent actinide and at least one trivalent lanthanide, and/or trivalent lanthanum and/or trivalent yttrium and, to provide an extraction agent which enables higher separating factors α to be obtained. It should therefore be possible to carry out the method at lower pH values or higher acid concentrations.

SUMMARY OF THE INVENTION

With the method and extraction agent of the invention it is possible at the same time to achieve a higher separation factor cx while maintaining extraction conditions at lower pH values or higher acid concentrations.

Advantageously further features of the invention are given in the dependent claims.

The invention will be elucidated below by way of example.

An aqueous phase contains trivalent ions of lanthanides (cerium (Ce), praseodymium (Pr), neodymium (Nd), promethium (Pr), samarium (Sm), europium (Eu), gadolinium (Gd), terbium (Tb), dysprosium (Dy), holmium (Ho), erbium (Er), thulium (Tm), ytterbium (Yb), luthenium (Lu), as well as lanthanum (La) and yttrium (Y) or at least one component of this group and ions of trivalent actinides, like americium (Am) and/or curium (Cm). The aqueous phase has a low pH value which can correspond to a $H^+$ concentration of a strong acid of 0.01 to 2 mole per liter. As acids, HCl, $H_2SO_4$ and especially $HNO_3$ can be used since $HNO_3$ forms readily soluble salts. The extraction is carried out by means of an organic solvent which contains as extraction medium bis(aryl)dithiophosphonic acid of the general formula (4)—$R_2PS(SH)$

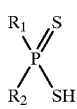

(4)

where:

$R_1$=phenyl or naphthyl, $R_2$=phenyl or naphthyl, as well as methyl-, ethyl-, propyl-, isopropyl-, cyano-, nitro-, halogenyl- (Cl—, F—, Br—, J—) substituted residues of $R_1$ and $R_2$ whereby $R_1$ and $R_2$ can be substituted with at least one of the components from the group of methyl, ethyl, propyl, isopropyl, cyano, nitro, halogenyl (Cl, F, Br, I).

This group are examples of substituents which increase the acidity of the extraction medium bis(aryl) dithiophosphonic acid and which contribute to especially good extraction results. What is important is the increase in the acidity of the extraction medium, the exact positions of the substituents being of less significance.

According to the invention, the organic phase contains at least one synergist from the group composed of trioctylphosphate (formula (5)), tris-(2-ethylhexyl)-phosphate (formula (6)) and tris-(2-propylpentyl)-phosphate (formula (7)).

(5)

(6)

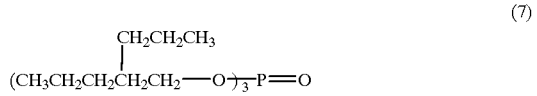

(7)

With the addition of the synergists according to the invention there is a significant increase in the separation phase α. The selectivity is significantly increased in the separation of the actinides from the lanthanides.

The organic solvent is advantageously a solvent containing aromatic components, like benzene, or a pure aromatic solvent.

In an especially advantageous rendering of the invention, at least one component is introduced into the solvent which is selected from the group which consists of toluene, xylol, tert.-butylbenzene, bis-(tert.-butyl)benzene or tris-(tert.-butyl)benzene, isopropylbenzene, bis-isopropylbenzene or tris-isopropylbenzene. The introduction of these solvents give rise to two additional positive side effects.

The first is a further increase in the selectivity of the $An^{3+}$ extraction and the other is an additional improvement in the coefficient distribution $D_{An(III)}$.

The effectiveness as to the separating factor and the distribution coefficient properties is in the following sequence: benzene<toluene<tert.-butylbenzene<bisisopropylbenzene, isopropylbenzene, tri-isopropylbenzene, bis-(tert. butyl-benzene), tris-(tert.butyl-benzene).

Below several examples are presented:
In the tables the results of the process of the invention are summarized:
It shows:
Table 1: The influence of synergists according to the invention upon the extraction.
Table 2: The influence of the solvents on the extraction.
Table 3: The composition of simulated actinide (III)—lanthanide (III) solutions working up for extraction investigations.
Table 4: The selective extraction of Am(III) from the simulated solutions of Table 3.

Test Description:
Chemicals and Extraction Medium
The chemicals tributylphosphate (Aldrich, 99%), TOPO (=trioctylphosphineoxide; Merck, p.a. quality), trimethylphosphate (Aldrich, 97%), triphenylphosphate (Aldrich, 98%), trihexylphosphate (Aldrich, 97%), trioctylphosphate (Alfa), tris(2-ethylhexyl)phosphate (Aldrich, 97%) are used as indicated. The solvents toluene, xylene, tert.- butylbenzene and triisoproplybenzene were of p.a. quality. The mixed lanthanide (III) solution of Ce(III), Eu(III), Gd(III), Nd(III), Pr(III), Sm(III), and Y(III), La(III) was prepared by weighing out their nitrate salts in $HNO_3$. An isotope tracer $Am^{241}$ (3.7 $Mb_q$ in 1 ml of 1 M Hcl) and Eu $^{152-154}$ (3.7 $Mb_q$ in 5 ml 0.5 M Hcl obtained from the Firm Blaseg was diluted to 100 ml with distilled $H_2O$. A 1:1 mixture of both solutions (pH 2) was used as the basic solution.

The aromatic dithiophosphonic acid was produced by the method of W. A. Higgins, P. W. Vogel, E. G. Craig, Journal of the American Chemical Society 77, 1864–1866 (1955). In good yields, apart from the described synthesis of bis (phenyldithiophosponic), the bis(methylphenyl), bis (chlorophenyl) and bis (fluorophenyl)dithiophosphonic acids were made. The extraction agent was produced by weighing out quantities of the dithiophosphonic acid and synergist and dissolving them in an aromatic solvent. The extraction experiments were carried out in centrifuge glasses with Teflon® stoppers. 2 mL of a nitric acid aqueous solution previously traced with Am-241 and Eu-152 were intensively mixed with 2 mL of the extraction agent. With centrifugation, the phases were separated and then aliquots each of 1 mL were taken from the organic and aqueous phases for analysis. The concentrations of the gamma nuclides Am-241 and Eu-152 were determined with the aid of gamma spectrometry. The concentrations of the inactive elements La, Ce, Pr, Nd, Sm, Eu, Gd and Y were determined with the aid of ICP-MS.

The following conditions apply to the data given in Tables 1–4:

Table 1

The influence of the synergist on the extraction of Am(III) and Eu(III) with a mixture of 0.5 mol/liter of bis (chlorophenyl)dithiophosphonic acid and 0.25 mol/liter of synergist in toluene from nitric acid.

Table 2

The influence of the solvent on the extraction of Am(III) and Eu(III) with a mixture of 0.5 mol/liter bis (chlorophenyl) dithiophosphonic and 0.25 mole/liter and trioctyiphosphinoxide from nitric acid solution.

Table 3

Composition of simulated actinide(III)—lanthanide(III) solutions of different $HNO_3$ concentrations from the reclaiming of nuclear fuels by the PUREX process for extraction tests (IV).

Table 4

The selective extraction of Am(III) from simulated actinide (III) solutions of different $HNO_3$ concentrations with a mixture of 0.5 mole/liter of bis(chlorophenyl) dithiophosphonic acid and 0.25 mol/liter of trioctylphosphenyl oxide in tert. butylbenzene.

The method of the invention and the extracting agent enable a highly effective separation of the trivalent radioactive reactor from the trivalent lanthanides which is especially desirable with radioactive reactive wastes.

TABLE 1

| Synergist (0.25 mol/liter) | 0.2 mol/liter $HNO_3$ | | |
|---|---|---|---|
| | $D_{Am}$ | $D_{Eu}$ | $\alpha_{Am/Eu}$ |
| Tributylphosphate | 2.13 | 0.068 | 31.2 |
| Trimethylphosphate | 0.0046 | 0.00037 | 12.3 |
| Triphenylphosphate | 0.0017 | 0.00022 | 8.1 |
| Trihexylphosphate | 25.54 | 21.25 | 1.2 |
| Trioctylphosphate | 2.11 | 0.0088 | 237.9 |
| Tris(2-ethylhexyl)phosphate | 1.98 | 0.00165 | 1199.8 |

TABLE 2

| Solvent | $HNO_3$ mol/liter | $D_{Am}$ | $D_{Eu}$ | $\alpha_{Am/Eu}$ |
|---|---|---|---|---|
| Toluene | 0.5 | 7.19 | 0.306 | 23.5 |
| | 1 | 0.794 | 0.0732 | 10.8 |
| | 2 | 0.113 | 0.0329 | 3.4 |
| | 3 | 0.0263 | 0.0158 | 1.7 |
| xylene | 0.5 | 8.83 | 0.385 | 22.9 |
| | 1 | 0.927 | 0.0805 | 11.5 |
| | 2 | — | — | — |
| | 3 | — | — | — |
| tert.-butylbenzene | 0.5 | 19.18 | 0.615 | 31.2 |
| | 1 | 1.768 | 0.0988 | 17.9 |
| | 2 | 0.193 | 0.0393 | 4.9 |
| | 3 | 0.0476 | 0.0219 | 2.2 |
| triisopropylbenzene | 0.5 | 55.8 | 1.23 | 45.6 |
| | 1 | 4.76 | 0.159 | 29.8 |
| | 2 | 0.416 | 0.057 | 7.3 |
| | 3 | 0.106 | 0.0461 | 2.3 |

TABLE 3

| | $HNO_3$ in mol/liter | | |
|---|---|---|---|
| | 0.5 | 0.99 | 2.06 |
| Element | in g/L | | |
| Y | 0.2372 | 0.2345 | 0.238 |
| La | 0.7446 | 0.72 | 0.7409 |
| Ce | 1.4595 | 1.383 | 1.447 |
| Pr | 0.6832 | 0.5993 | 0.6715 |
| Nd | 2.4823 | 2.455 | 2.4948 |
| Sm | 0.4806 | 0.4685 | 0.4796 |
| Eu | 0.0939 | 0.0878 | 0.0907 |
| Gd | 0.0751 | 0.0765 | 0.0813 |
| Am-241 | Tracer Quantities | | |

TABLE 4

| | $HNO_3$ | | | | | |
|---|---|---|---|---|---|---|
| | 0.5 mol/l | | 1.0 mol/l | | 2.0 mol/l | |
| Element | $D_{M(III)}$ | $\alpha_{Am/Ln}$ | $D_{M(III)}$ | $\alpha_{Am/Ln}$ | $D_{M(III)}$ | $\alpha_{Am/Ln}$ |
| Y | 0.325 | 36.7 | 0.0384 | 43.6 | <0.005 | — |
| La | 0.254 | 46.9 | 0.0353 | 47.4 | 0.0053 | 33.8 |
| Ce | 0.551 | 21.6 | 0.0741 | 22.6 | 0.006 | 29.8 |
| Pr | 0.527 | 22.6 | 0.0844 | 19.9 | 0.0135 | 13.3 |
| Nd | 0.296 | 40.3 | 0.0527 | 31.8 | 0.0099 | 18.1 |
| Sm | 0.373 | 31.9 | 0.0627 | 24.9 | 0.0099 | 18 |
| Gd | 0.303 | 39.4 | 0.0515 | 32.5 | 0.0082 | 21.8 |
| Eu | 0.357 | 33.4 | 0.0688 | 24.4 | 0.0122 | 14.8 |
| $^{152}$Eu | 0.352 | 33.8 | 0.0931 | 18 | 0.0377 | 4.8 |
| $^{241}$Am | 11.926 | | 1.677 | | 0.18 | |

What is claimed is:

1. A method of separating at least one trivalent actinide element from at least one trivalent lanthanide element and/or yttrium in an aqueous acidic solution containing said elements, said method comprising the steps of:
   (a) maintaining an $H^+$ concentration of said solution in a range of 0.01 moles/liter to 2 moles/liter; and
   (b) extracting said solution at said $H^+$ concentration of 0.01 moles/liter to 2 moles/liter with an extractant which consists essentially of:
   (1) a compound of the Formula (4)

(4)

wherein
   $R_1$=phenyl or naphthyl,
   $R_2$=phenyl or naphthyl, or $R_1$ and $R_2$ are each phenyl or naphthyl substituted by methyl, ethyl, propyl, isopropyl, cyano, nitro, or halogen,
   (2) an extraction synergist selected from the group consisting of trioctylphosphate, tris-(2-propylpentyl)-phosphate, and tris-(2-ethylhexyl)-phosphate; and
   (3) an organic solvent or solvent mixture.

2. The method defined in claim 1 wherein the organic solvent is an aromatic compound.

3. The method defined in claim 2 wherein the aromatic solvent is a compound selected from the group consisting of toluene, xylene, tert.-butylbenzene, bis-(tert.-butyl)-benzene, tris-(tert.-butyl)-benzene, isopropylbenzene, bis-(isopropyl)-benzene and tris-(isopropyl)benzene.

4. The method defined in claim 1 wherein the trivalent actinide elements americum and curium are separated from the trivalent lanthanide elements.

5. The method defined in claim 1 wherein at least one of the trivalent actinide elements and trivalent lanthanide elements is radioactive.

6. An extraction medium which consists essentially of:
   (1) a compound of the Formula (4)

(4)

wherein
   $R_1$=phenyl or naphthyl,
   $R_2$=phenyl or naphthyl, or $R_1$ and $R_2$ are each phenyl or naphthyl substituted by methyl, ethyl, propyl, isopropyl, cyano, nitro, or halogen,
   (2) an extraction synergist selected from the group consisting of trioctylphosphate, tris-(2-propylpentyl)-phosphate, and tris-(2-ethylhexyl)-phosphate; and
   (3) an organic solvent or solvent mixture.

7. The extraction medium defined in claim 6 wherein the organic solvent is an aromatic compound.

8. The extraction medium defined in claim 7 wherein the aromatic solvent is a compound selected from the group consisting of toluene, xylene, tert.-butylbenzene, bis-(tert.-butyl)-benzene, tris-(tert.-butyl)-benzene, isopropylbenzene, bis-(isopro-pyl)-benzene and tris-(isopropyl)benzene.

* * * * *